United States Patent [19]

Sole

[11] 4,367,744
[45] Jan. 11, 1983

[54] MEDICAL INSTRUMENT, AND METHOD OF UTILIZING SAME

[76] Inventor: Gary M. Sole, 510 Overbrook, Bloomfield Hills, Mich. 48013

[21] Appl. No.: 221,065

[22] Filed: Dec. 29, 1980

[51] Int. Cl.³ .............................................. A61B 17/38
[52] U.S. Cl. .................................. 128/303.1; 219/236
[58] Field of Search ........... 128/303.1, 303.13, 303.14, 128/303.17; 219/227, 229, 233, 236, 237, 238

[56] References Cited

U.S. PATENT DOCUMENTS

| | | | |
|---|---|---|---|
| 1,919,543 | 7/1933 | Doane | 128/303.17 |
| 2,033,397 | 3/1936 | Richman | 128/303.17 |
| 2,844,697 | 7/1958 | Emmerson | 219/233 X |
| 3,884,237 | 5/1975 | O'Malley | 128/303.14 |
| 4,108,181 | 8/1978 | Sclianis | 128/303.1 |

OTHER PUBLICATIONS

Peyman et al, "Experimental Intraocular Coagulation", Opthelmic Surgery, Jan.-Feb., 1972, vol. 3, No. 1, pp. 32-37.

Gorsch, "Biopsy in Proctology", American J of Surgery, p. 484, Jun. 1936.

Primary Examiner—Lee S. Cohen
Attorney, Agent, or Firm—Irving M. Weiner; Pamela S. Burt; John L. Shortley

[57] ABSTRACT

A medical instrument including a cautery portion for use in performing an anterior capsulotomy during extracapsular cataract extraction surgery. A substantially rigid stem portion is connected between the cautery portion and a handle portion, and is provided with bends to facilitate maneuverability of the cautery portion and to avoid substantial interference with the surgical field of vision by the handle portion. An electrical path is defined through the handle portion and stem portion to the cautery portion so as to permit electrical current to be supplied to the cautery portion so as to rapidly heat same to a burning temperature so as to burn a circle in the anterior lens capsule of the eye during surgery. The stem portion and handle portion are covered with an electrically-insulative material.

12 Claims, 7 Drawing Figures

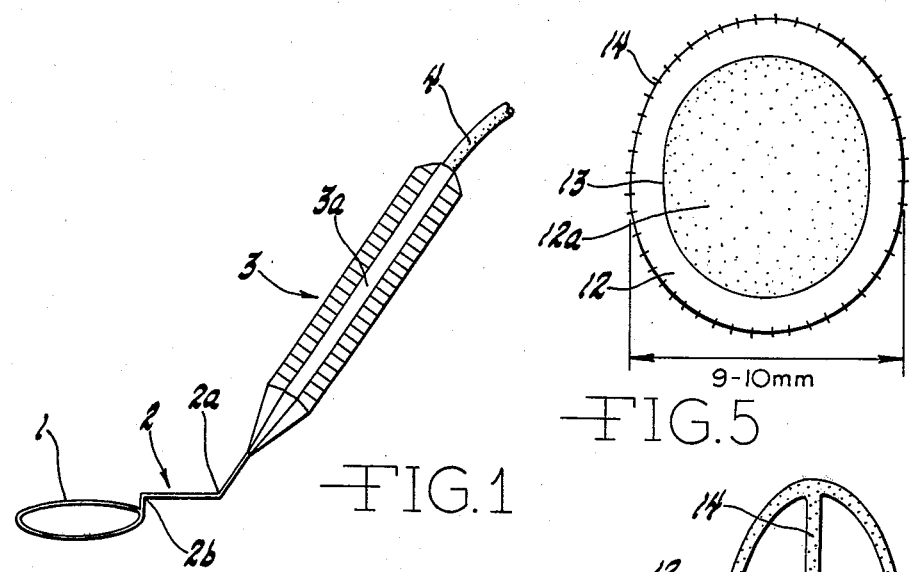
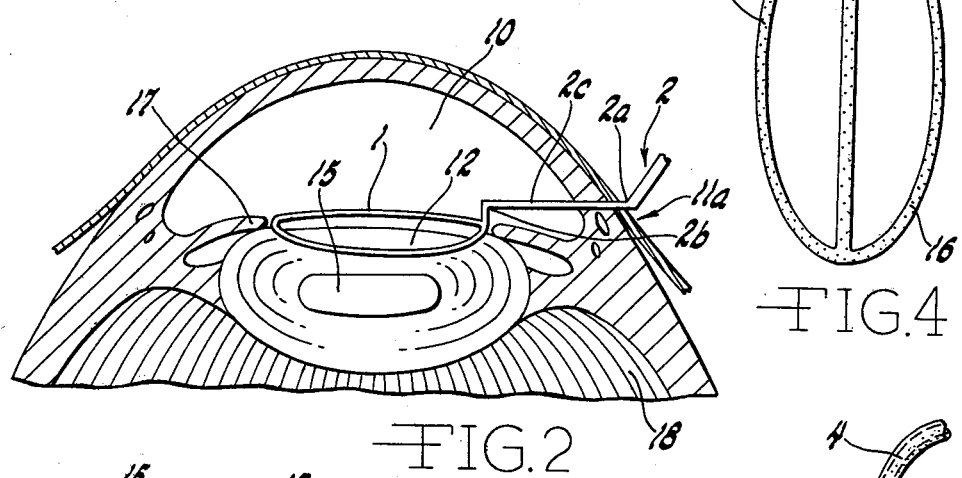
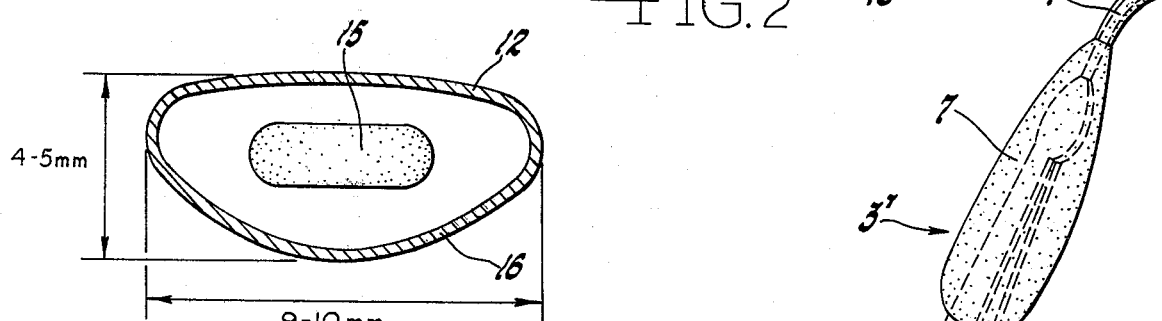
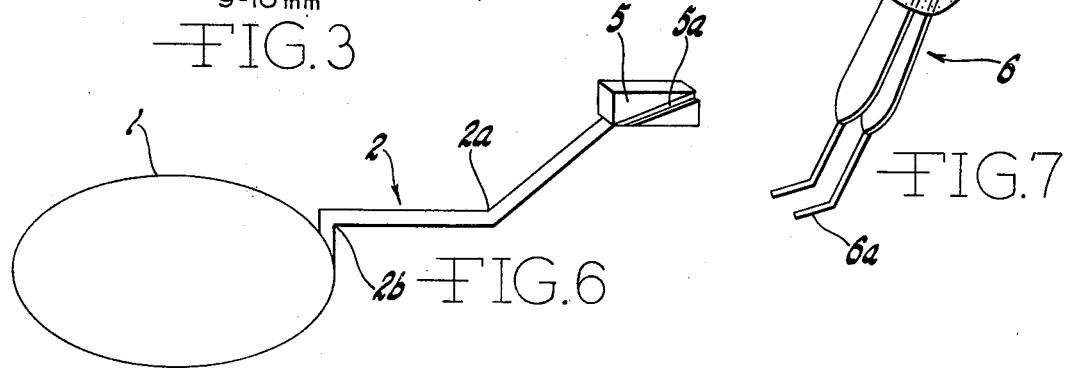

MEDICAL INSTRUMENT, AND METHOD OF UTILIZING SAME

BACKGROUND OF THE INVENTION

1. Field of the Invention

The present invention relates generally to a medical instrument for use in performing extracapsular cataract surgery, and a method for utilizing the medical instrument in performing such surgery.

More particularly, the invention relates to a medical instrument for use in performing an arterior capsulotomy during extracapsular cataract surgery. The medical instrument in accordance with the invention includes a wire cautery portion having a substantially circular shape which is connected with an electrical power source so as to heat the cautery portion to a burning temperature. In performing a capsulotomy during extracapsular cataract surgery, the cautery portion is positioned in contact with the anterior lens capsule so as to burn a circle therein to thus permit removal of a circular portion of the anterior lens capsule.

2. Description of Relevant Art

The human eye includes a lens having the configuration of a biconvex disc. The lens surface comprises a capsule which includes an anterior capsule and a posterior capsule which meet at an equator. Zonules extending from the ciliary body are attached to the lens equator so as to secure the lens in position. Disposed within the lens capsule is a softer cortex and a firm inner nucleus.

In a healthy human eye, the lens is formed of a clear crystalline protein, however, the lens will at times opacify to form what is known as a cataract. When it is required to remove the cataract, the surgical procedure generally employed heretofore by operating surgeons is known as in intracapsular cataract extraction. Such procedure entails making a 180° incision at the superior limbus of the eye, retracting the iris, contacting the superior anterior lens capsule with an iceball (a cryoprobe), and extracting the entire lens within its capsule while separating same from the surrounding zonules.

In recent times, with the advent of the intraocular lenses, the surgical microscope and phacoemulsification, many eye surgeons have come to prefer a surgical procedure known as extracapsular cataract extraction. In such procedure, the eye is opened at the superior limbus, and either hooks, scissors or special forceps are employed to open the anterior lens capsule and express from within the capsule the nucleus of the lens. Thereafter, the remaining cortical material is removed so as to thus leave a clear posterior lens capsule in the eye, which capsule provides a barrier between the anterior chamber and the vitreous cavity of the eye.

Many factors are involved in attempting to successfully perform the extracapsular surgical method. One such factor resides in successful removal of a large portion of the anterior lens capsule, i.e., a capsulatomy, which facilitates access to the lens nucleus and removal of the cortical material. A hazard associated with such a capsulotomy is any contact between the anterior and posterior lens capsules, which results in adherence together of the anterior and posterior capsules and opacification of the posterior capsule. Accordingly, and because the lens capsule is highly elastic and the edges thereof roll and curl after the capsule has been cut, successful performance of a perfect capsulotomy is difficult.

Various methods have heretofore been employed for performing a capsulotomy during extracapsular cataract surgery. In one such method which has been commonly employed, a hooked needle (cystotome) is introduced into the eye at the limbus, and a 360° incision is made at the periphery of the anterior capsule. In other known methods, the capsulotomy is performed with instruments such as scissors or special forceps. However, such known methods have attendant disadvantages due to the difficulties encountered in attempting to manipulate the aforesaid instruments within the very limited confines of the anterior chamber of the eye. Accordingly, there has developed a desideratum for a surgical instrument and technique for performing an anterior capsulotomy during extracapsular cataract surgery which overcomes the shortcomings and disadvantages attendant known instruments and techniques.

The present invention effectively overcomes the various disadvantages associated with known anterior capsulotomy instruments and techniques by providing a medical instrument including a cautery portion which is heated by an electrical current to a burning temperature so as to burn a very vlean and uniform circle in the anterior lens capsule. The resultant effect is similar to that of a branding iron, and permits ready removal of the portion of the anterior lens capsule within the burned circle to complete the capsulotomy and permit the remainder of the extracapsular surgical method to be performed.

Some of the various attempts which have been made in the general field of cautery-type or heated-type medical instruments include: the "Dental Instrument" disclosed in U.S. Pat. No. 1,335,987 issued in 1920 to Reid et al; the "Therapeutic Appliance" disclosed in U.S. Pat. No. 1,615,828 issued in 1927 to Chesney; the "Means for Effecting the Bloodless Removal of Diseased Tissue" disclosed in U.S. Pat. No. 1,919,543 issued in 1933 to Doane; and the "Device for Removing Excrescences and Polyps" disclosed in U.S. Pat. No. 4,202,338 issued in 1980 to Bitrolf. However, none of such known medical instruments are structurally or functionally suitable for use in eye surgery, and particularly for an anterior capsulotomy to be performed during extracapsular cataract surgery.

SUMMARY OF THE INVENTION

The present invention provides a medical instrument including cautery means for burning an anterior lens capsule of an eye at the periphery of a portion of said capsule to be removed during surgery, a handle portion, and a substantially rigid elongated stem portion extending from the cautery means and connected with the handle portion, the stem portion being electrically-conductive and covered with an electrically-insulative material. Means are provided for connecting the cautery means, via the electrically-conductive stem portion, with an electrical power source. The cautery means preferably comprises a substantially circular-shaped wire cautery portion having an overall diameter corresponding to the diameter of a circular portion to be removed from the anterior lens capsule during eye surgery, i.e., during an anterior capsulotomy. Preferably, the stem portion comprises a substantially rigid wire covered with electrically-insulative material along the length thereof and formed with an obtuse angular bend in an intermediate portion thereof between the cautery portion and the handle portion and a right angular bend in a first end portion thereof adjacent the wire cautery portion.

The end portion of the stem portion which is connected to the handle portion may be either fixedly or removably secured thereto such that the electrically-conductive stem portion is in electrical contact with an electrical conductor extending through the handle portion.

In a second embodiment of the invention, the handle portion comprises electrified forceps covered with electrically-insulative material, an end portion of the stem portion is secured to an intermediate connecting portion, and the intermediate connecting portion is provided with receiving portions adapted to removably receive therein the operating tips of the electrified forceps. The receiving portions of the intermediate connecting portion are provided with electrical contacts operatively connected between the end portion of the stem portion and the tips of the electrified forceps.

The present invention further provides a method for utilizing the aforesaid medical instrument in performing extracapsular cataract surgery, and particularly for performing an anterior capsulotomy. In accordance with such method, the pupil of an eye to be operated upon is dilated, and the wire cautery portion of the medical instrument is introduced into the eye. The cautery portion is positioned in contact with the surface of the anterior lens capsule of the eye, and an electrical current is applied from the power source to the cautery portion to heat the cautery portion to a burning temperature so as to burn a circle in the anterior lens capsule. The portion of the anterior lens capsule within the burned circle is then removed, and the extracapsular cataract surgery can then be continued.

It is an object of the present invention to provide a medical instrument including a fine wire cautery portion which can be readily manipulated by means of a bent stem portion connected with a handle portion, and which effects a clean, uniform circular burn in the anterior lens capsule to ensure successful performance of a capsulotomy during extracapsular cataract surgery.

The above and other objects, details and advantages of the present invention will become apparent from the following detailed description, when read in conjunction with the accompanying drawings.

BRIEF DESCRIPTION OF THE DRAWINGS

FIG. 1 is a perspective view of a medical instrument in accordance with a first embodiment of the present invention.

FIG. 2 is a sectioned side view of a human eye during a surgical procedure employing the medical instrument in accordance with the invention.

FIG. 3 is a sectioned side view of a lens of a human eye.

FIG. 4 is a side view of a lens capsule of a human eye.

FIG. 5 is a top plan view of an anterior lens capsule showing a portion thereof to be removed during a capsulotomy.

FIG. 6 is a perspective view of a wire cautery portion with attached stem and connecting portions of a medical instrument in accordance with a second embodiment of the invention.

FIG. 7 is a perspective view of a handle portion for connection with the connecting portion of FIG. 6 in accordance with the second embodiment of the invention.

DETAILED DESCRIPTION OF PREFERRED EMBODIMENTS

With reference to FIG. 1, the medical instrument in accordance with a first embodiment of the present invention includes a cautery portion 1, an elongated stem portion 2 interconnected at a first end thereof with the cautery portion 1 and at a second end thereof with a handle portion 3, and an electrical conductor 4 connected to the upper end of handle portion 3.

The handle 3 is substantially elongate and may have a generally cylindrical shape, or any other desired suitable shape. Handle 3 is fabricated of an electrically-insulative material such as plastic or the like, and is provided with an electrical conductor or wire 3a extending therethrough. The electrical conductor 4 attached to the upper end of handle 3 may comprise an extension of conductor 3a or alternatively may comprise a separate wire electrically connected with conductor 3a, and is covered with an electrically-insulative material. If desired, conductor 4 may be removably attached to the upper end of handle 3 by suitable connecting means. Conductor 4 is provided at the free end thereof with a suitable plug (not shown) for connection with an electrical power source (not shown).

The elongated stem portion 2 may have the second end thereof either fixedly secured to the lower end of handle 3, or removably secured thereto by suitable connecting means. In this regard it will be understood that by removably securing stem portion 2 to handle 3, the combined stem and cautery portions of the instrument may be considered as a disposable unit. Alternatively, if desired, the entire instrument may be provided in a disposable form.

Stem portion 2 is substantially rigid, and is fabricated of an electrically conductive material such as a length of wire, covered along the length thereof with an electrically-insulative material, with the outside diameter of stem portion 2 being as small as possible. The second end of stem portion 2 connected to handle 3 is in electrical contact with conductor 3a of handle 3, such that an electrically-conductive path is defined from conductor 4, through handle 3 (via conductor 3a), and through stem portion 2 to the first end thereof secured to cautery portion 1. The stem portion 2 is provided with an obtuse angular bend 2a in an intermediate portion thereof, which is bent at an angle of approximately 120°, for example. At the first end portion thereof adjacent cautery portion 1, stem portion 2 is provided with a substantially right angular bend 2b. Such bend portions 2a and 2b are provided in order to minimize interference with the surgical field of vision, particularly by handle portion 3, and to facilitate manipulation of cautery portion 1 when the medical instrument is being employed for use during surgery.

The wire cautery portion 1 is integrally connected with the first end of stem portion 2 in electrical contact therewith, and is formed of a substantially rigid or shape-retentive wire which is as fine as possible while still being capable of reaching a suitable temperature for burning the anterior lens capsule of an eye in the presence of aqueous material, such temperature being in the range of, for example, 500° C. to 2000° C. The cautery portion 1 has a substantially circular shape, or may be formed to have other shapes so as to correspond to a peripheral part of the portion of the capsule to be removed, as desired by the surgeon. The overall diameter of cautery portion 1 is dependent upon the diameter of the pupil of the particular eye upon which surgery is to be performed, and the present invention thus contemplates providing medical instruments according to the invention with cautery portions 1 of varying diameters. Preferably, the medical instruments would be provided with cautery portions 1 having varying diameters of from 6 mm to 9 mm provided in 0.5 mm increasing incremental sizes to provide the surgeon with a desirable selection of cautery portion sizes. In this regard, the stem portion 2 for the cautery portion 1 will have a length dimension dependent upon the diameter size of the cautery portion, as will be described in greater detail hereinbelow.

A surgical technique utilizing the medical instrument as thus far described in performing extracapsular cataract surgery, and particularly in performing an anterior capsulotomy during extracapsular cataract surgery, will now be described hereinbelow with reference to FIGS. 2-5.

In FIG. 2, the cautery portion 1 is shown as introduced into the anterior chamber 10 of the eye at the limbus portion 11a of the cornea. The pupil of the eye is maximally dilated to permit positioning of cautery portion 1 in contact with the surface of the anterior lens capsule 12 without contacting other ocular structure. With cautery portion 1 thus positioned in contact with the surface of anterior lens capsule 12 as shown in FIG. 2, electrical current is then applied to cautery portion 1 via conductor 4, conductor 3a, and electrically-conductive stem portion 2. The very fine wire cautery portion 1 is rapidly heated by such applied current for an instant so as to burn a clean, substantially perfect and uniform circle 13 in the anterior capsule 12, as shown in FIG. 5. It will thus be understood that the medical instrument in accordance with the invention functions in a manner analogous to a conventional branding iron, although much more delicately, in burning the circle 13 in anterior lens capsule 12. After the circle 13 has been burning in the anterior lens capsule 12 by means of cautery portion 1, the surgeon then removes portion 12a (FIG. 5) of anterior lens capsule 12 within circle 13, i.e., by washing it out. Thereafter, the extracapsular cataract surgery is continued (with the use of forceps and/or other suitable instruments) by expressing from within the lens capsule the nucleus 15 of the lens (FIGS. 2 and 3) and removing the remaining cortical material so as to leave only a clear posterior lens capsule 16 (FIGS. 2-4) within the eye to serve as a barrier between the anterior chamber and the vitreous cavity.

The medical instrument as described hereinabove should be fabricated so as to be very light in overall construction, so as to avoid excessive posterior pressure on the lens during the anterior capsulotomy. Further, consideration should be given to the overall construction and the material forming the various component portions of the instrument to ensure that the very fine wire cautery portion 1 will reach its burning temperature as rapidly as possible, maintain such temperature only long enough to burn the circle 13, and then rapidly cool. In this regard, it will be understood that any suitable switches and/or other electrical circuitry components may be employed to effect the aforesaid rapid heating and cooling characteristics.

Because the electrically-conductive stem portion 2 is covered with an electrically-insulative material as described hereinabove, it will be understood that inadvertent burning of the iris 17, cornea 11 or sclera 18 (FIG. 2) by such stem portion 2 will be effectively avoided.

With further regard to stem portion 2, the dimension thereof in the straight portion 2c between bends 2a and 2b is determined such that the obtuse angular bend 2a will be located just outside of the cornea 11 during the capsulotomy, as shown in FIG. 2, to thus facilitate manipulation and positioning of the cautery portion 1 within the anterior chamber 10. Accordingly, it will be understood that such dimension of stem portion 2c is substantially inversely proportional to the overall diameter of cautery portion 1, with longer lengths thereof being required with cautery portions of smaller diameters. By way of example, for a 9 mm diameter cautery portion 1, a suitable length for stem portion 2c would be approximately 4 mm.

With reference to FIGS. 4 and 5, designated at 14 are the zonular attachments disposed at the equator at which the anterior and posterior lens capsules meet, and attaching from the ciliary body so as to secure the lens in position.

In accordance with a second embodiment of the invention as shown in FIGS. 6 and 7, the first end of stem portion 2 is connected with cautery portion 1 as described hereinabove in connection with the first embodiment of the invention, however, the second end of stem portion 2 is secured to an intermediate connecting portion 5. Connecting portion 5 is formed of an electrically-insulative material and is shown in FIG. 6 as having a box shape, however, it will be understood that connecting portion 5 may have any desired shape. A pair of receiving portions or grooves 5a are provided in connecting portion 5 and have electrical contact points provided therein and electrically connected with the inner electrically-conductive portion (wire) of stem portion 2. If desired, connecting portion 5 may be connected with a suitable electrical conductor for direct connection to an electrical power source (not shown).

With reference to FIG. 7, there is shown a handle portion 3' in accordance with the second embodiment of the invention. Handle portion 3' is constructed mainly of McPherson Forceps 6 which may be connected via electrical conductor 4 to an electrical power source (not shown). A covering 7 of electrically-insulative material is disposed over the forceps 6 to define a hand grip portion, with the lower operating tips 6a of the forceps extending therefrom. The tips 6a may be inserted within the receiving portions 5a of connecting portion 5 (FIG. 6), and the receiving portions 5a are particularly adapted in size and shape to securely respectively receive operating tips 6a therein. Upon insertion of tips 6a within receiving portions 5, an electrical path will be established from conductor 4, through forceps 6, through the contacts in portions 5a, and through stem portion 2 to cautery portion 1. When desired, the tips 6a of forceps 6 may be slidably removed from receiving portions 5a, and thereafter employed separately as a surgical instrument. It will thus be understood that the medical instrument in accordance with the second embodiment of the invention provides a dual-instrument capacity, and if desired the portion of the instrument shown in FIG. 6 including cautery portion 1 may be disposed with after use.

Although there have been described what are at present considered to be the preferred embodiments of the invention, it will be understood that the invention may be embodied in other specific forms without departing from the spirit or essential characteristics thereof. The present embodiments are therefore to be considered in all respects as illustrative, and not restrictive. The scope of the invention is indicated by the appended claims rather than by the foregoing description.

I claim:

1. A medical instrument, comprising:
   cautery means for burning the anterior lens capsule of an eye at the periphery of a portion of said capsule to be removed during surgery;
   said cautery means comprising a cautery portion formed of a fine wire and shaped so as to correspond to a peripheral part of said portion of said capsule to be removed;
   a handle portion;
   a substantially rigid elongated stem portion extending from said cautery portion and connected with said handle portion, said stem portion being electrically-conductive and covered with an electrically-insulative material;
   said cautery portion having a dimension corresponding to the diameter of the pupil of an eye to be operated upon;
   said stem portion having a dimension which is substantially inversely proportional to said dimension of said cautery portion; and
   means for connecting said cautery portion, via said electrically-conductive stem portion, with an electrical power source.

2. A medical instrument according to claim 1, wherein:
   said cautery portion has a substantially circular shape.

3. A medical instrument according to claim 2, wherein:
   said stem portion comprises a substantially rigid wire covered with said electrically-insulative material along the length thereof; and
   said stem portion is formed with an obtuse angular bend in an intermediate portion thereof between said cautery portion and said handle portion.

4. A medical instrument according to claim 3, wherein:
   said stem portion is formed with a right angular bend in a first end portion thereof adjacent said wire cautery portion.

5. A medical instrument according to claim 3, wherein:
   the length of said stem portion from a first end portion adjacent said wire cautery portion to said obtuse angular bend is substantially equal to or greater than 4 mm.

6. A medical instrument according to claim 2, wherein:
   said means for connecting said cautery portion with an electrical power source includes an electrical conductor extending through said handle portion and connected with said electrically-conductive stem portion; and
   said handle portion is fabricated of an electrically-insulative material surrounding said electrical conductor.

7. A medical instrument according to claim 6, wherein:
   an end portion of said stem portion is fixedly secured to said handle portion in electrical contact with said electrical conductor.

8. A medical instrument according to claim 6, wherein:
   an end portion of said stem portion is removably secured to said handle portion so as to be in electrical contact with said electrical conductor.

9. A medical instrument according to claim 1, wherein:
   said handle portion comprises electrified forceps provided with a covering of electrically-insulative material;
   an end portion of said stem portion is secured to an intermediate connecting portion;
   said intermediate connecting portion is provided with receiving portions within which the operating tips of said electrified forceps are removably received; and
   said receiving portions of said intermediate connecting portion are provided with electrical contacts operatively connected between said end portion of said stem portion and said tips of said electrified forceps.

10. A medical instrument according to claim 1, wherein:
    said cautery portion has a substantially circular shape; and
    said dimension of said cautery portion comprises a diammetrical dimension of between substantially 6 mm and 9 mm.

11. A medical instrument according to claim 1, wherein:
    said stem portion is formed with an obtuse angular bend in an intermediate portion thereof between said cautery portion and said handle portion, and a right angular bend in a first end portion thereof adjacent said wire cautery portion; and
    said dimension of said stem portion comprises the length of a straight part of said stem portion extending between said obtuse angular bend and said right angular bend.

12. A method for utilizing a medical instrument in performing extracapsular cataract surgery, comprising the steps of:
    dilating the pupil of an eye to be operated upon;
    holding a handle portion of said medical instrument while introducing a cautery means of said medical instrument into said eye, said cautery means being connected to said handle portion by means of a substantially rigid elongated stem portion extending from said cautery means and connected with said handle portion, said stem portion being electrically conductive and covered with an electrically-insulative material;
    positioning said cautery means in contact with the periphery of a portion of the anterior lens capsule of said eye;
    applying electrical current from an electrical power source to said cautery means, via said electrically-conductive stem portion, to heat said cautery means to a burning temperature, so as to burn said anterior lens capsule at said periphery of said portion of said capsule; and
    removing the anterior lens capsule portion within said peripheral burn.

* * * * *